United States Patent

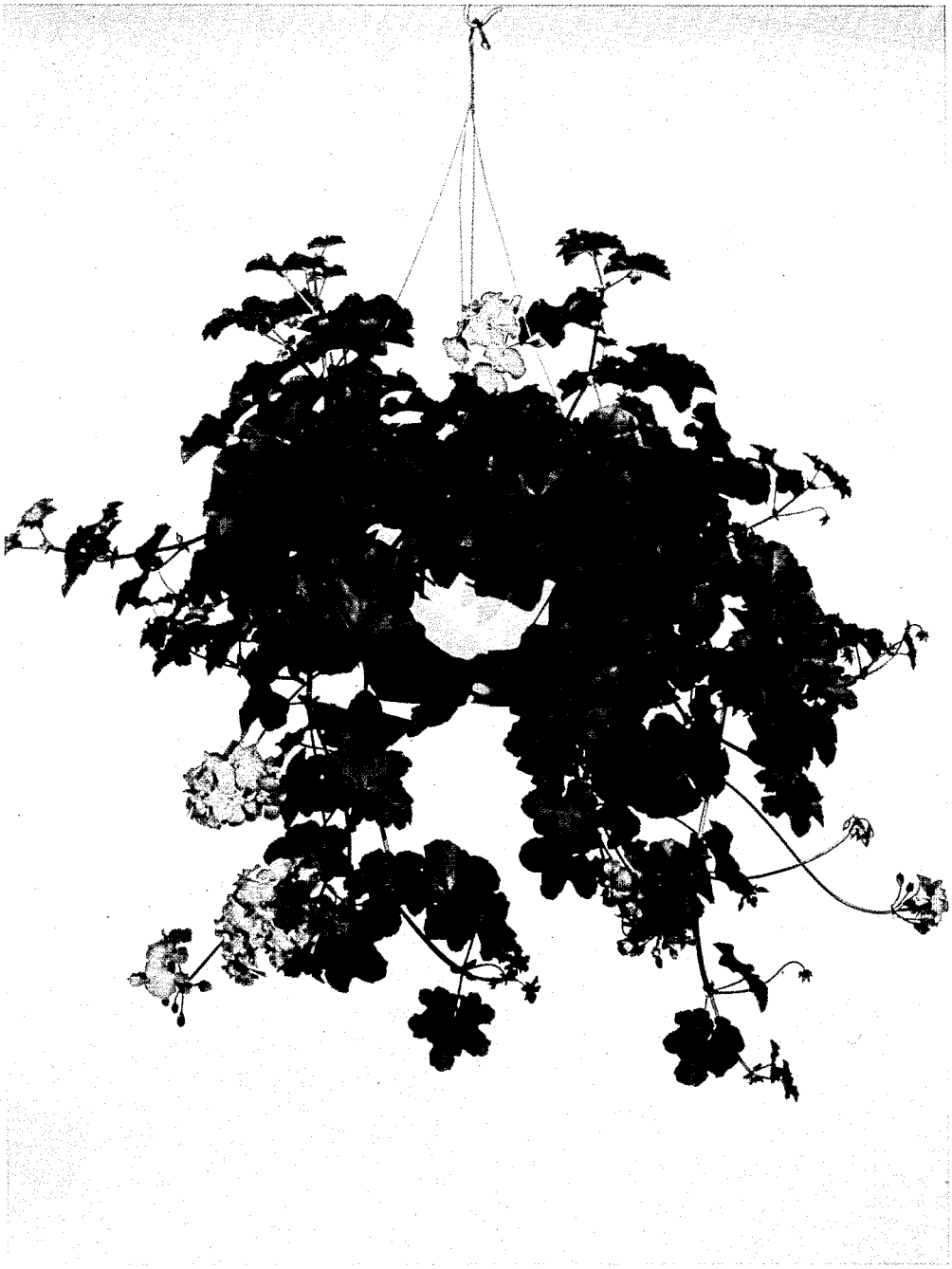

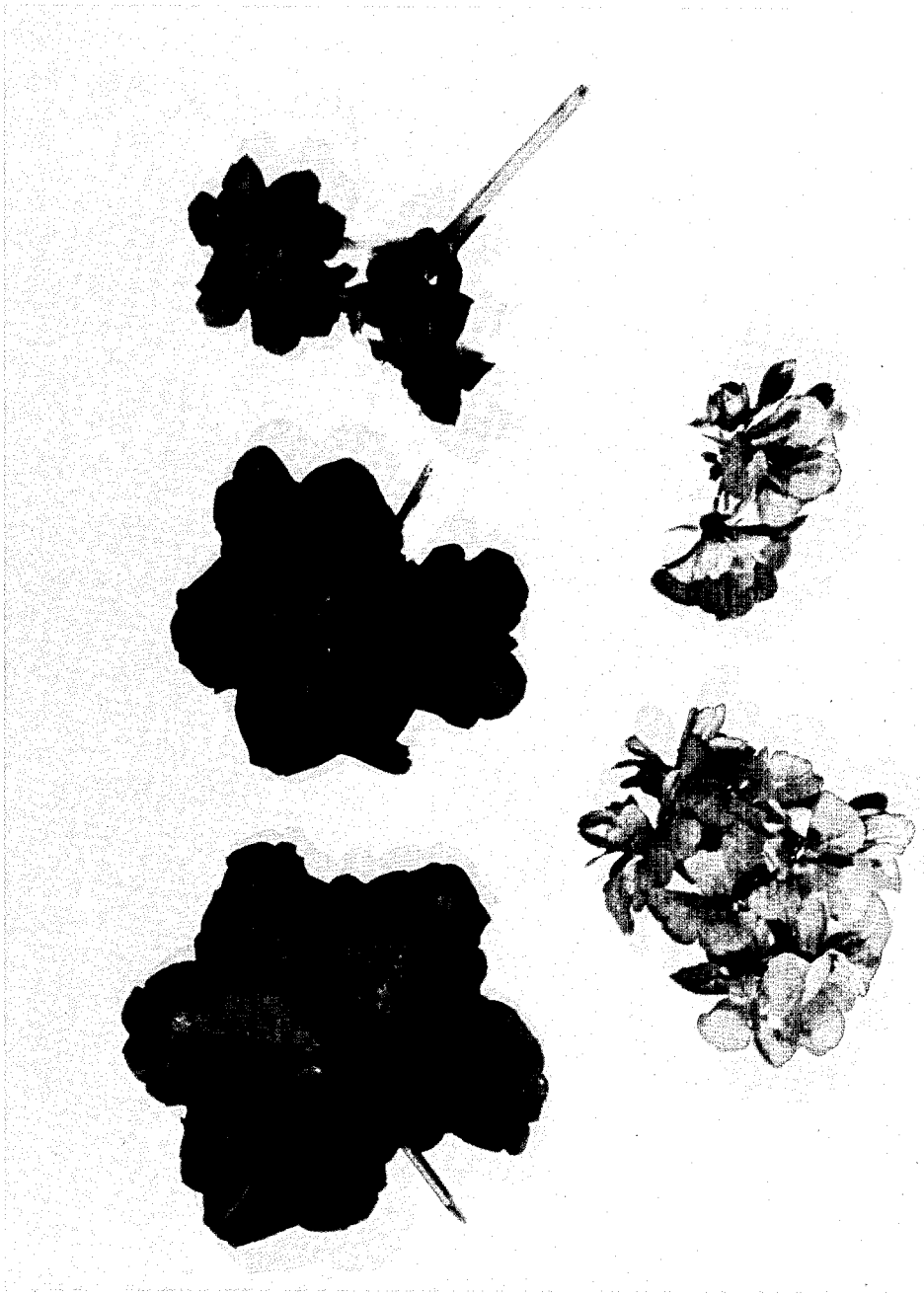

Plant Pat. 3,874
Patented Apr. 27, 1976

3,874

GERANIUM PLANT

William E. Duffett, Akron, Ohio, and Walter W. Knicely, Inwood, W. Va., assignors to Yoder Brothers, Inc., Barberton, Ohio

Filed Mar. 6, 1975, Ser. No. 556,126
Int. Cl. A01h *5/00*
U.S. Cl. Plt.—68 1 Claim

The present invention comprises a new and distinct cultivar of *Pelargonium peltatum,* Ait, hereinafter referred to as Yale (#72105004).

Yale was originated from a cross made under the supervision of William E. Duffett and Walter W. Knicely in a controlled breeding program in Barberton, Ohio in the year 1971.

The male or pollen parent, was Cayucas (unpatented; commercially available), an ivy geranium of fuchsia pink color of unknown parentage.

The female, or seed parent, was Mexican Beauty (unpatented; commercially available), an ivy geranium of crimson red color of unknown parentage.

Yale was discovered and selected as a flowering seedling within the progeny of the stated cross by William E. Duffett and Walter W. Knicely on Aug. 17, 1972 in a controlled environment in Barberton, Ohio.

Yale is a product of a planned breeding program which had the objective of creating an ivy geranium that would fulfill in part or in whole the need for intensified dark red flower color, increased color retention and increased tolerance of Ohio light and temperature for continuous outdoor summer flowering.

The first act of asexual reproduction of Yale was accomplished when vegetative cuttings were taken from the initial seedling in September 1972 in a controlled environment in Barberton, Ohio by a technician according to formulations established and supervised by William E. Duffett and Walter W. Knicely.

Continued asexual reproduction by vegetative cuttings for evaluative tests in flowering and stock programs in conjunction with horticultural certification initiated June 18, 1973 in Barberton, Ohio have demonstrated that the combination of characteristics as herein disclosed for Yale are firmly fixed and are retained through successive generations of asexual reproduction.

The following descriptive observations, measurements, and comparisons were derived from plants grown both in a greenhouse and under outdoor lath conditions. The greenhouse-grown, spring-flowered containerized plants were moved to an outdoor lath location in late May, early June and observed during the summer and fall months. The environmental conditions under which the plants were grown closely approximate those generally used in commercial practice and are described in Chart A. A light intensity chart of general use is shown in Figure 14.14 in ASHAE Trans., Vol. 64, page 64, and reference is made thereto.

The following traits have been repeatedly observed and are determined to be basic characteristics of Yale which in combination distinguished this ivy geranium as a new and distinct cultivar:

(1) Dark red flower color with minimal color oxidation.

(2) Prolific flowering traits under outdoor summer conditions in Ohio.

(3) Medium green glossy foliage.

(4) Vigorous trailing growth with long internode length.

(5) Fair foliage durability with slight breakdown under outdoor summer conditions in Ohio.

The accompanying colored photographic drawings show typical flower and foliage characteristics of Yale. Sheet 1 comprises a photograph of Yale in bloom, and sheet 2 comprises a photograph showing the development of the inflorescence and the foliage of Yale. It is noted that difficulty was encountered in obtaining photographs accurately representing the true colors of Yale. The actual flower color of Yale is closely approximated in sheet 1. Sheet 2 approximates both the flower and foliage color of Yale, but is too intense and dark in color. The color readings are, however, correct.

The phenotype of Yale may vary significantly with variations in environment such as temperature, light intensity, and daylength outside the described ranges. The genotype of Yale was not observed under all possible environments.

Of the many commercial cultivars known to the present inventors the most similar existing cultivars in comparison to Yale are the parental cultivars Mexican Betuty and Cayucas. Reference is made to attached Chart B which compares certain characteristics of Mexican Beauty and Cayucas with those same characteristics of Yale. General comparisons are as follows:

(1) In comparison to Mexican Beauty, Yale has more intense red flower color with less blue tones and less color oxidation, more prolific outdoor summer flowering traits, and less durable outdoor summer foliage characteristics. The growth habit, internode length, and the flower form of Yale are similar to those of Mexican Beauty.

(2) In comparison to Cayucas, Yale has dark red flower color, more vigorous (more trailing) growth habit, longer internode length, more prolific outdoor summer flowering traits, and less durable outdoor summer foliage characteristics. The flower form of Yale is similar to that of Cayucas.

In the following description, all color references are to the Munsell Limit Color Cascade, 1972 edition. The notation (a) indicates that the color values were determined between 2:00 p.m. and 2:30 p.m. on July 22, 1974 under 150 foot candle light intensity at Barberton, Ohio. The notation (b) indicates that the color values were determined between 1:00 p.m., and 1:30 p.m. on Sept. 30, 1974, under 25 foot candle light intensity at Barberton, Ohio.

Botanical classification: *Pelargonium peltatum*, Ait., cv Yale.

I. INFLORESCENCE

A. *Umbel*:
- *Average Diameter*: 3.5 inches.
- *Peduncle*: Ranges from 2.5 inches to 4.5 inches in length, averaging 3.5 inches.
- *Pedicel*: 0.75 inch to 1.1 inches in length, averaging 1 inch.

B. *Corolla*:
- *Average Diameter*: 1.8 inches.
- *Type*: Semi-double; rotate.
- *Color* (*a*): Abaxial: 40–12. Adaxial: 40–10. Blotch: 40–16.

C. *Bud*:

- *Shape*: Conodial.
- *Color* (*a*): Abaxial: 40–12. Adaxial: 39–10. Blotch: 40–16.

D. *Reproductive Organs*:
- *Androecium*: Stamen: monodelphous; dorsifixed. Pollen: present.

E. *Response Period*: Early.

F. *Production*: Good.

| Date: | Average number of flowers |
|---|---|
| July 15, 1974 | 12 |
| Aug. 1, 1974 | 20 |
| Aug. 15, 1974 | 38 |
| Sept. 1, 1974 | 20 |

G. *Durability*:
- *Shatter resistance*: Poor.
- *Tolerance of botrytis*: Good.

II. PLANT

A. *Foliage*:
- *Form*: Reni-form.
- *Margin*: Undulate.
- *Color* (b): Abaxial: 21–13 to 21–14. Adaxial: 21–12 overlaid with white.
- *Durability* (*outdoor*): Good.

B. *Growth Habit*:
- *Form*: Trailing.
- *Height*: Vigorous.
- *Internode length*: Long.

C. *Durability*:
- *Tolerance of botrytis*: Good.

CHART A—ENVIRONMENT FOR IVY GERANIUM PERFORMANCE EVALUATION COMMONLY USED IN BARBERTON, OHIO

| | Environment | |
|---|---|---|
| | I. Greenhouse | II. Outdoor lath (30% light reduction) |
| Period of year | February through May | June through September |
| Temperature (° F.) | Night, 62–65; Bright day, 72–75; Cloudy day, 68–70 | Uncontrolled dependent on prevailing weather conditions. |
| Light | Uncontrolled dependent upon natural daylength and light intensity. Light shade compound on greenhouse glass. | Uncontrolled dependent upon natural daylength and light intensity. 30% intensity reduction from lath. |
| Schedule and specifications. | Take vegetative cutting—February 19. Cutting specification—2–2.75 inches in length. Direct stick—February 20; 5 cuttings per 10 inch basket. Media—1 part soil, 1 part peat, 1 part perlite. Pinch—every 4 nodes to finish April 10. Flower—May 28. | Move to outdoor lath location—early June (product produced in I). |

CHART B—COMPARISON OF YALE WITH MEXICAN BEAUTY AND CAYUCAS

| Cultivar | Flower color | Growth habit | Internode length | Outdoor flowering traits | Flower form | Outdoor Foliage durability |
|---|---|---|---|---|---|---|
| Yale | Dark red | Vigorous and trailing | Long | Excellent | Semidouble | Fair. |
| Mexican Beauty | Crimson red | do | do | Fair | do | Good. |
| Cayucas | Fuchsia pink | Compact and spreading | Medium | do | do | Do. |

NOTE.—Comparisons made of plants grown in a greenhouse and under outdoor lath in Barberton, Ohio under conditions described in Chart A.

We claim:

1. A new and distinct cultivar of geranium plant characterized particularly by its red flower color with minimal color oxidation, prolific flowering traits under outdoor summer conditions in Ohio, medium green glossy foliage, vigorous trailing growth habit with long internode length, and by its fair foliage durability with slight breakdown under outdoor summer conditions in Ohio.

No references cited.

ROBERT E. BAGWILL, Primary Examiner